US012667328B2

(12) United States Patent (10) Patent No.: US 12,667,328 B2
Mirar et al. (45) Date of Patent: Jun. 30, 2026

(54) SYSTEM FOR CATHETER-GUIDED VISUALIZATION AND RENDERING

(71) Applicant: GE Precision Healthcare LLC, Waukesha, WI (US)

(72) Inventors: Hani Nozari Mirar, Oslo (NO); Olivier Gerard, Oslo (NO)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/887,776

(22) Filed: Sep. 17, 2024

(65) Prior Publication Data

US 2026/0076643 A1     Mar. 19, 2026

(51) Int. Cl.
| A61B 8/08 | (2006.01) |
| A61B 8/00 | (2006.01) |
| G06T 7/20 | (2017.01) |
| G06T 7/70 | (2017.01) |
| A61M 25/01 | (2006.01) |

(52) U.S. Cl.
CPC ............ A61B 8/0841 (2013.01); A61B 8/461 (2013.01); G06T 7/20 (2013.01); G06T 7/70 (2017.01); *A61M 2025/0166* (2013.01); *G06T 2207/10136* (2013.01); *G06T 2207/20104* (2013.01); *G06T 2207/30021* (2013.01)

(58) Field of Classification Search
CPC ......... A61B 8/0841; A61B 8/461; G06T 7/20; G06T 7/70
See application file for complete search history.

(56) References Cited

U.S. PATENT DOCUMENTS

| 10,299,753 | B2 | 5/2019 | Govari et al. |
| 10,772,606 | B2 | 9/2020 | Kim et al. |
| 10,835,210 | B2 | 11/2020 | Ralovich et al. |
| 11,217,000 | B2 | 1/2022 | Dala-Krishna |
| 11,850,338 | B2 | 12/2023 | Misener |
| 2009/0005687 | A1* | 1/2009 | Kawae ................. A61B 8/0833 |
| | | | 600/461 |

(Continued)

OTHER PUBLICATIONS

Jia et al., A Hybrid Catheter Localisation Framework in Echocardiography Based on Electromagnetic Tracking and Deep Learning Segmentation, Oct. 2022.

(Continued)

*Primary Examiner* — Andrew W Begeman
(74) *Attorney, Agent, or Firm* — SPQ IP LLC

(57) ABSTRACT

Various systems and methods are provided for generating an ultrasound image of a region of interest of a subject including a medical instrument and a delineation of a predicted impact point of the medical instrument. Ultrasound data of the region of interest of the subject may be acquired. The position of the medical instrument in the region of interest of the subject may be determined. The predicted impact point of the medical instrument with respect to an anatomical feature of the region of interest of the subject may be determined based on the position of the medical instrument and the ultrasound data of the region of interest of the subject. The ultrasound image of the region of interest of the subject including the medical instrument and the delineation of the predicted impact point of the medical instrument may be generated and displayed.

20 Claims, 14 Drawing Sheets

(56)  References Cited

U.S. PATENT DOCUMENTS

| | | | | |
|---|---|---|---|---|
| 2013/0041250 | A1* | 2/2013 | Pelissier | A61B 8/461 |
| | | | | 600/424 |
| 2020/0375664 | A1* | 12/2020 | Tang | A61B 34/20 |
| 2021/0100627 | A1 | 4/2021 | Soper et al. | |
| 2021/0169583 | A1 | 6/2021 | Gleiman | |
| 2022/0104886 | A1* | 4/2022 | Blanchard | A61B 17/3403 |
| 2022/0409172 | A1 | 12/2022 | Govari et al. | |
| 2023/0139348 | A1* | 5/2023 | Ishrak | A61F 2/2427 |
| | | | | 600/424 |
| 2024/0050060 | A1* | 2/2024 | Kadokura | A61B 8/0841 |

OTHER PUBLICATIONS

Ralovich et al., 6DoF Catheter Detection, Application to Intracardiac Echocardiography, 2014.

* cited by examiner

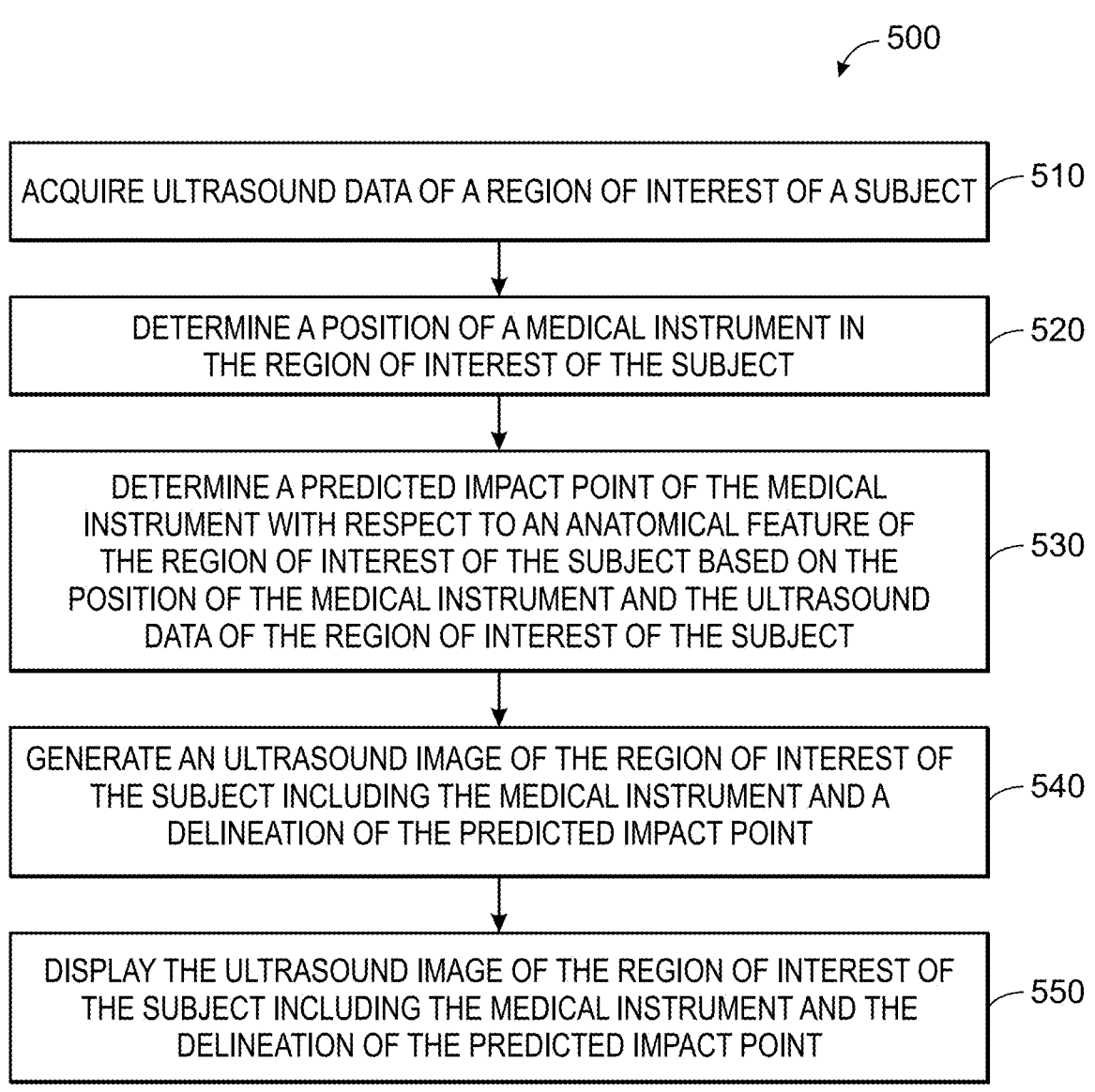

500

ACQUIRE ULTRASOUND DATA OF A REGION OF INTEREST OF A SUBJECT ⎯ 510

DETERMINE A POSITION OF A MEDICAL INSTRUMENT IN
THE REGION OF INTEREST OF THE SUBJECT ⎯ 520

DETERMINE A PREDICTED IMPACT POINT OF THE MEDICAL
INSTRUMENT WITH RESPECT TO AN ANATOMICAL FEATURE OF
THE REGION OF INTEREST OF THE SUBJECT BASED ON THE
POSITION OF THE MEDICAL INSTRUMENT AND THE ULTRASOUND
DATA OF THE REGION OF INTEREST OF THE SUBJECT ⎯ 530

GENERATE AN ULTRASOUND IMAGE OF THE REGION OF INTEREST OF
THE SUBJECT INCLUDING THE MEDICAL INSTRUMENT AND A
DELINEATION OF THE PREDICTED IMPACT POINT ⎯ 540

DISPLAY THE ULTRASOUND IMAGE OF THE REGION OF INTEREST OF
THE SUBJECT INCLUDING THE MEDICAL INSTRUMENT AND THE
DELINEATION OF THE PREDICTED IMPACT POINT ⎯ 550

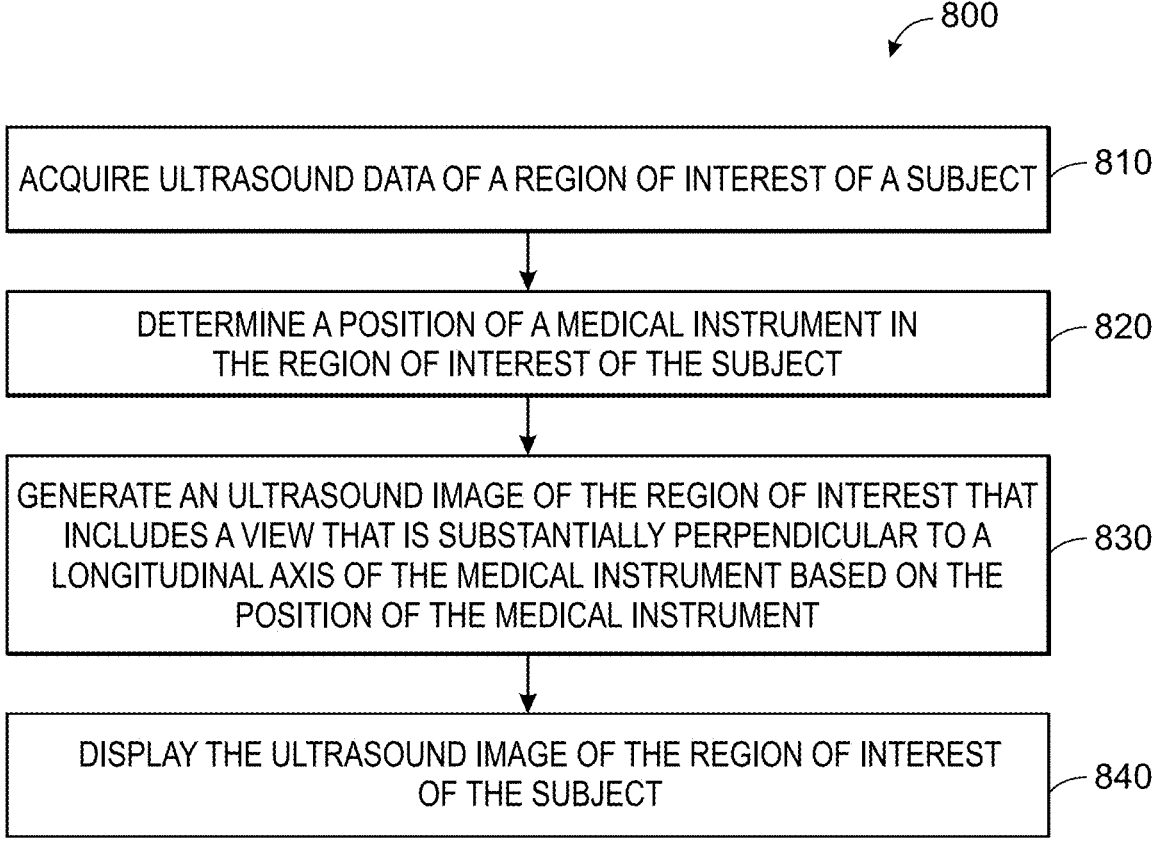

800

ACQUIRE ULTRASOUND DATA OF A REGION OF INTEREST OF A SUBJECT — 810

DETERMINE A POSITION OF A MEDICAL INSTRUMENT IN
THE REGION OF INTEREST OF THE SUBJECT — 820

GENERATE AN ULTRASOUND IMAGE OF THE REGION OF INTEREST THAT
INCLUDES A VIEW THAT IS SUBSTANTIALLY PERPENDICULAR TO A
LONGITUDINAL AXIS OF THE MEDICAL INSTRUMENT BASED ON THE
POSITION OF THE MEDICAL INSTRUMENT — 830

DISPLAY THE ULTRASOUND IMAGE OF THE REGION OF INTEREST
OF THE SUBJECT — 840

FIG. 8

900
904
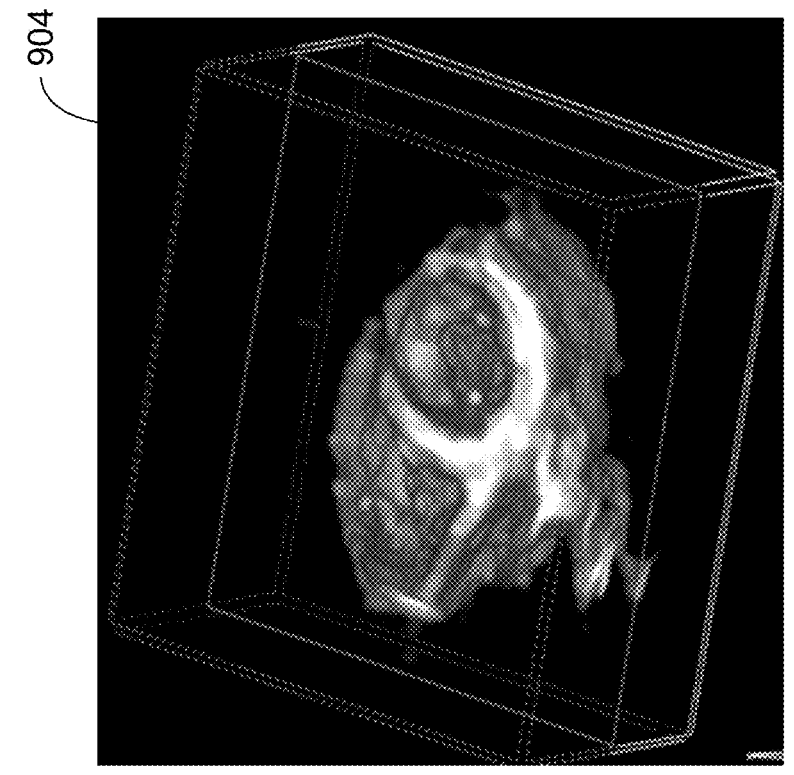
902
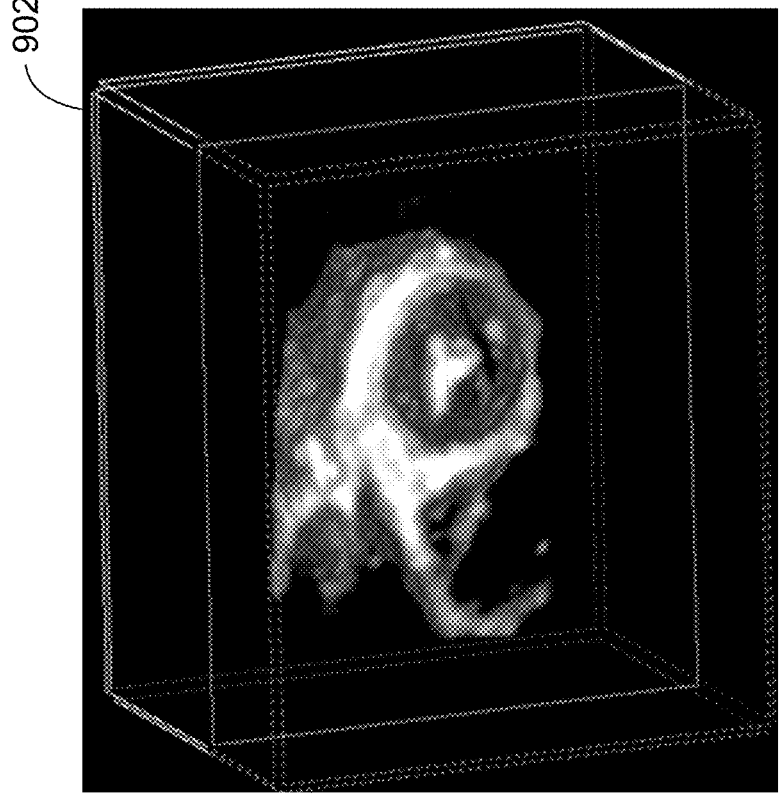
FIG. 9

1000
1004
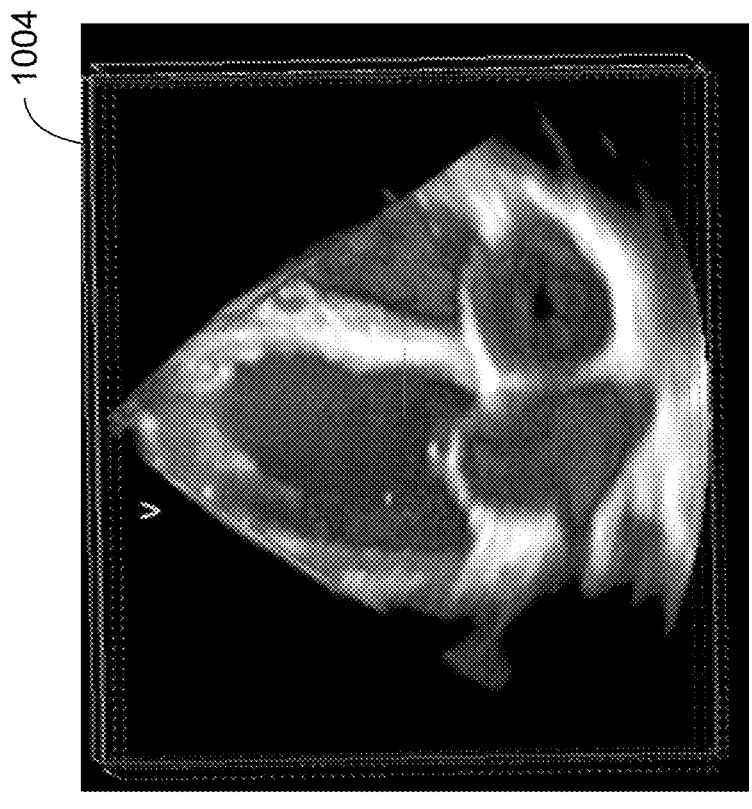
1002
FIG. 10

SYSTEM FOR CATHETER-GUIDED VISUALIZATION AND RENDERING

TECHNICAL FIELD

The present disclosure relates, generally, to a system and method for generating ultrasound images of a region of interest and a tracked medical instrument provided in the region of interest. More specifically, the present disclosure relates to a system and method for determining a predicted impact point of the medical instrument with respect to an anatomical feature of the region of interest of a subject, and generating an ultrasound image of the region of interest of the subject including the medical instrument and a delineation of the predicted impact point of the medical instrument.

BACKGROUND

During an interventional procedure, an operator might navigate a medical instrument through a region of interest of a subject. In some cases, the operator might be required to position the medical instrument near, or in contact with, a specific anatomical feature. For instance, during a cardiac procedure, a clinician may navigate a medical instrument (e.g., a catheter) through a heart of a subject in order to ablate tissue, insert a mitral valve clip, close a left atrial appendage, deliver a stent, remove a thrombus, analyze cardiac function, or the like. As an example, an operator might contact cardiac tissue with an ablation catheter to ablate the cardiac tissue. As another example, the operator might position a catheter near the mitral valve to attach a mitral valve clip to the mitral valve. As another example, the operator might position a catheter near the left atrial appendage to insert a device to block the left atrial appendage, to clamp the left atrial appendage, or to suture the left atrial appendage. The precise positioning of the medical instrument relative to these various anatomical structures improves safety of the subject and improves the likelihood of the success of the interventional procedures.

Moreover, the region of interest may include various features that the medical instrument should not contact, or come into close proximity with, in order to maintain safety of the subject. For example, in thermal ablation implementations, the close proximity of an ablation catheter to a permanent pacing device might increase the risk of pacing dysfunctions for both pacemakers and defibrillators. As another example, the His bundle, which travels through the membranous septum in immediate proximity to the posterior sinus of the Valsalva and runs just under the left ventricular endocardium, is anatomically vulnerable to mechanical trauma during catheterization. A single touch of these structures by a catheter tip may cause intra-His bundle injury resulting in complete heart blockage. As another example, manipulation of a catheter within the heart may inadvertently dislodge thrombi. As another example, utilizing an improper technique or aggressively manipulating a cardiac catheter may result in injuries to the internal walls or valves of the heart. Accordingly, the operator should be cognizant of the positioning of the medical instrument relative to these susceptible anatomical features.

An ultrasound imaging system may acquire ultrasound images of the region of interest and the medical instrument, and display the ultrasound images to assist the operator in navigating the medical instrument through the region of interest. In some cases, the ultrasound imaging system may generate and display three-dimensional (3D) ultrasound images that depict the position of the medical instrument relative to various anatomical features of the region of interest. These 3D ultrasound images may assist the operator to position the medical instrument relative to various anatomical features and/or to avoid various anatomical features. In some cases, the operator might manually adjust the view of the ultrasound images in order to ascertain the positioning of the medical instrument in the region of interest. However, this manual adjustment might be non-intuitive, might introduce delays during interventional procedures, or the like. In other cases, the operator might not be able to ascertain the anatomical features that are positioned along the trajectory of the medical instrument. In these cases, the operator might not be able to assess where the medical instrument should be positioned, or may inadvertently contact, or come into close proximity with, a susceptible anatomical feature.

SUMMARY

This summary introduces concepts that are described in more detail in the detailed description. It should not be used to identify essential features of the claimed subject matter, nor to limit the scope of the claimed subject matter.

In an aspect, a system may include a memory configured to store instructions; and one or more processors configured to execute the instructions to: acquire ultrasound data of a region of interest of a subject; determine a position of a medical instrument in the region of interest of the subject; determine a predicted impact point of the medical instrument with respect to an anatomical feature of the region of interest of the subject based on the position of the medical instrument and the ultrasound data of the region of interest of the subject; generate an ultrasound image of the region of interest of the subject including the medical instrument and a delineation of the predicted impact point of the medical instrument; and display the ultrasound image of the region of interest of the subject including the medical instrument and the delineation of the predicted impact point of the medical instrument.

In another aspect, a method may include acquiring ultrasound data of a region of interest of a subject; determining a position of a medical instrument in the region of interest of the subject; determining a predicted impact point of the medical instrument with respect to an anatomical feature of the region of interest of the subject based on the position of the medical instrument and the ultrasound data of the region of interest of the subject; generating an ultrasound image of the region of interest of the subject including the medical instrument and a delineation of the predicted impact point of the medical instrument; and displaying the ultrasound image of the region of interest of the subject including the medical instrument and the delineation of the predicted impact point of the medical instrument.

In yet another aspect, a non-transitory computer-readable medium may store instructions that, when executed by one or more processors, cause the one or more processors to: acquire ultrasound data of a region of interest of a subject; determine a position of a medical instrument in the region of interest of the subject; determine a predicted impact point of the medical instrument with respect to an anatomical feature of the region of interest of the subject based on the position of the medical instrument and the ultrasound data of the region of interest of the subject; generate an ultrasound image of the region of interest of the subject including the medical instrument and a delineation of the predicted impact point of the medical instrument; and display the ultrasound image of the region of interest of the subject including the medical instrument and the delineation of the predicted impact point of the medical instrument.

BRIEF DESCRIPTION OF DRAWINGS

FIG. 5 is a flowchart of an example process for generating an ultrasound image of a region of interest of a subject including a medical instrument and a delineation of a predicted impact point of the medical instrument.

FIG. 8 is a flowchart of an example process for generating an ultrasound image of a region of interest of a subject including a view that is substantially perpendicular to a longitudinal axis of a medical instrument in the region of interest.

FIGS. 9-11 are diagrams of an example user interface that displays an ultrasound image of a region of interest of a subject including a view that is substantially perpendicular to a longitudinal axis of a medical instrument in the region of interest.

DETAILED DESCRIPTION

As addressed above, an operator may navigate a medical instrument through a region of interest of a subject during an interventional procedure, and might desire to carefully position the medical instrument near, or away from, certain anatomical features. However, the displayed ultrasound images of the region of interest and the medical instrument might not be readily intuitive for the operator, and/or the operator might not be able to readily assess where the medical instrument should be positioned, or may inadvertently contact, or come into close proximity with, a susceptible anatomical feature using the medical instrument.

Some embodiments herein determine a predicted impact point of a medical instrument with respect to an anatomical feature of a region of interest of a subject, and generate an ultrasound image of the region of interest of the subject including the medical instrument and a delineation of the predicted impact point of the medical instrument. In this way, some embodiments herein provide an improvement to ultrasound imaging and an improvement to the ultrasound images by providing a delineation of a predicted impact point of the medical instrument. Further, some embodiments herein improve subject safety during interventional procedures, reduce the time of interventional procedures, improve the efficacy of interventional procedures, etc., by improving the intuitiveness of the generated and displayed ultrasound images.

Figure 1:
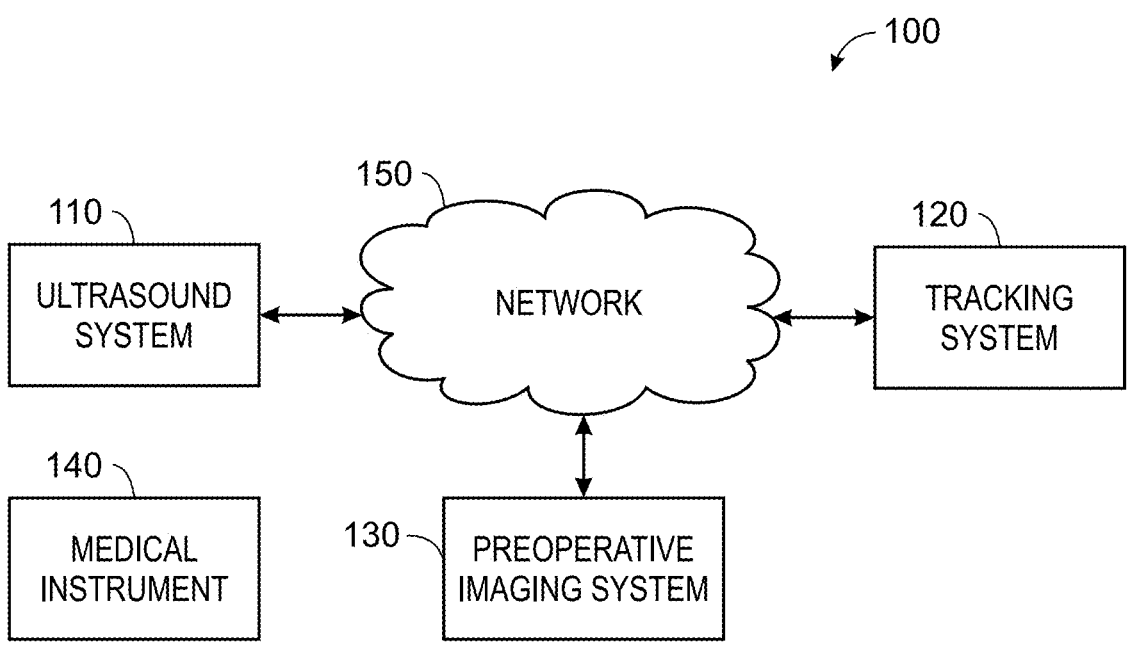
FIG. 1 is a diagram of an example system for generating an ultrasound image of a region of interest of a subject including a medical instrument and a delineation of a predicted impact point of the medical instrument.

FIG. 1 is a diagram of an example system 100 for generating an ultrasound image of a region of interest of a subject including a medical instrument and a delineation of a predicted impact point of the medical instrument. As shown in FIG. 1, the system 100 may include an ultrasound system 110, a tracking system 120, a preoperative imaging system 130, a medical instrument 140, and a network 150.

The ultrasound system 110 may be configured to acquire ultrasound data of a region of interest of a subject. For example, the ultrasound system 110 may be a two-dimensional (2D) ultrasound system, a three-dimensional (3D) ultrasound system, a four-dimensional (4D) ultrasound system, a Doppler ultrasound system, or the like. The subject may be a person, an animal, a phantom, or the like. The region of interest may be any anatomical region of the subject. For example, the region of interest may be a heart, a brain, an organ, a blood vessel, or the like. The ultrasound system 110 may use transesophageal echocardiography (TEE), intracardiac echocardiography (ICE), transthoracic echocardiography (TTE), or the like.

The tracking system 120 may be configured to acquire tracking data of the medical instrument 140 located within the region of interest of the subject. For example, the tracking system 120 may be an electromagnetic tracking system, an optical tracking system, an acoustic tracking system, an inertial tracking system, an ultrasound tracking system, or the like.

The preoperative imaging system 130 may be configured to acquire preoperative imaging data of the region of interest of the subject. For example, the preoperative imaging system 130 may be a computed tomography (CT) system, a magnetic resonance imaging (MRI) system, an ultrasound system, an X-ray system, a positron emission tomography (PET) device, or the like.

The medical instrument 140 may be any medical instrument that can be navigated through a region of interest of a subject. For example, the medical instrument 140 may be a catheter, a needle, a trocar, a cannula, or the like. The medical instrument 140 may be used for various interventional procedures involving the region of interest. For example, a catheter may be used for delivering a stent to an occluded blood vessel, inserting a mitral valve clip, closing a left atrial appendage, ablating tissue, analyzing cardiac function, removing a thrombus from an occluded blood vessel, or the like. Alternatively, the medical instrument 140 may be an implantable device that is to be implanted in the heart of the subject. For example, the implantable device may be a pacemaker, a stent, a defibrillator, a left ventricular assist device, a valve clip, or the like. Alternatively, the medical instrument 140 may be any object that can be navigated throughout the region of interest and/or tracked through the region of interest.

The network 150 may permit communication between the ultrasound system 110, the tracking system 120, and the preoperative imaging system 130. For example, the network 150 may be a local area network (LAN), a wide area network (WAN), a metropolitan area network (MAN), a cellular network, a private network, an ad hoc network, an intranet, the Internet, a fiber optic-based network, a wired network, a wireless network, or the like, and/or a combination of these or other types of networks.

The number and arrangement of the system 100 are provided as an example. In practice, the system 100 may include additional systems, fewer systems, different systems, or differently arranged systems than those shown in FIG. 1. Additionally, or alternatively, a set of systems (e.g., one or more systems) of the system 100 may be integrated into a single system, and/or perform one or more functions described as being performed by another system, or set of systems, of the system 100.

Figure 2:
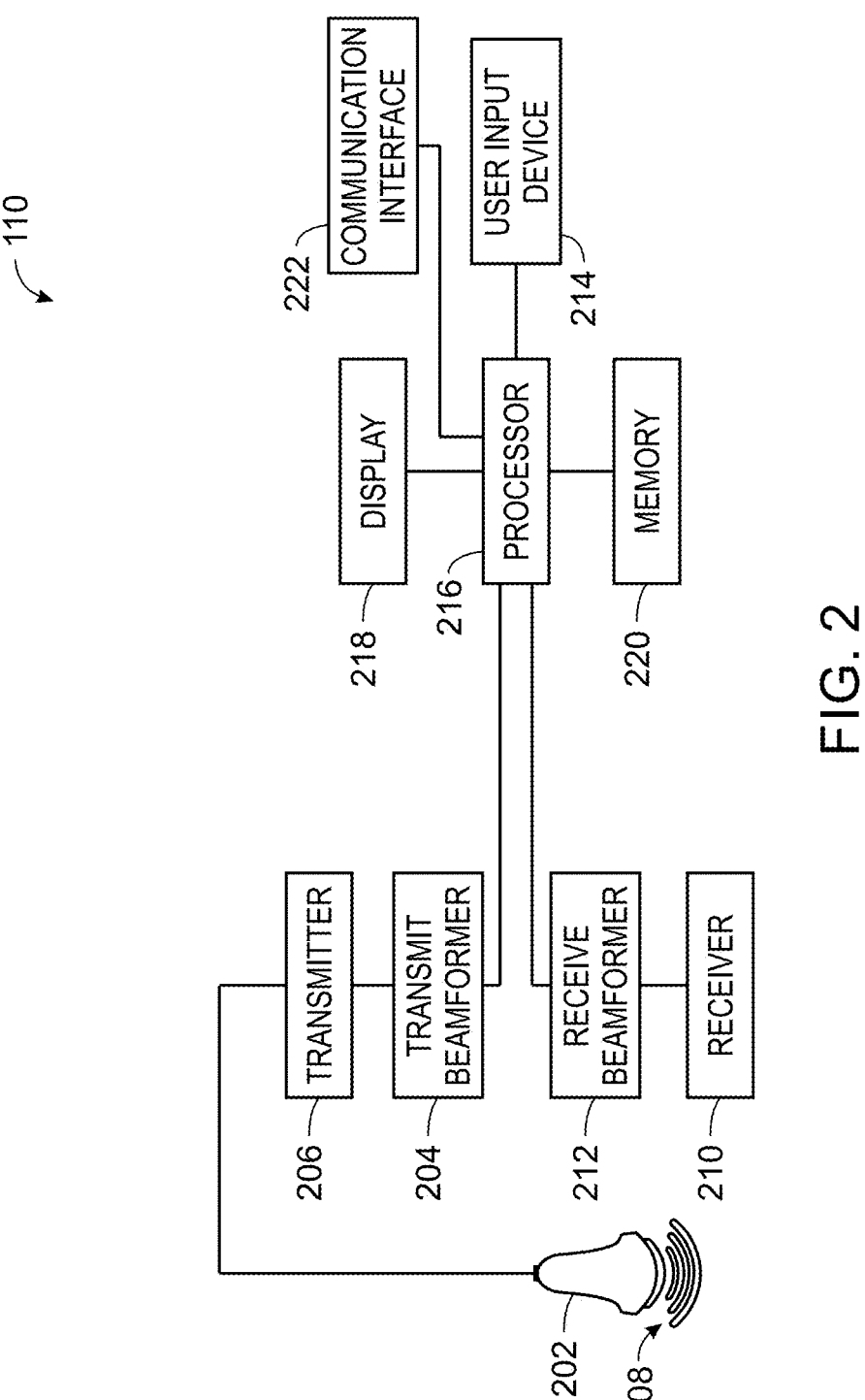
FIG. 2 is a diagram of an example ultrasound system for generating an ultrasound image of a region of interest of a subject including a medical instrument and a delineation of a predicted impact point of the medical instrument.

FIG. 2 is a diagram of example components of the ultrasound system 110 for generating an ultrasound image of a region of interest of a subject including a medical instrument and a delineation of a predicted impact point of the medical instrument. As shown in FIG. 2, the ultrasound system 110 may include an ultrasound probe 202, a transmit beamformer 204, a transmitter 206, elements 208 a receiver 210, a receive beamformer 212, a user input device 214, a processor 216, a display 218, a memory 220, and a communication interface 222. The foregoing components may be connected via wired or wireless connections.

The ultrasound probe 202 may be configured to acquire ultrasound data. For example, the ultrasound probe 202 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4D (e4D) probe, a low profile wearable patch version of any of the foregoing probes, or the like. According to an embodiment, the ultrasound probe 202 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data. The ultrasound data may be 4D ultrasound data, 3D ultrasound data, 2D ultrasound data, or the like.

The transmit beamformer 204 may be configured to apply delay times to electrical signals provided to the elements 208 to focus corresponding ultrasound signals at the region of interest. The transmitter 206 may be configured to transmit electrical signals to the elements 208 to drive the elements 208 to emit ultrasound signals towards the region of interest. The elements 208 may be configured to receive the electrical signals from the transmitter 206, convert the electrical signals into ultrasound signals, and emit the ultrasound signals towards the region of interest. The elements 208 may be configured to receive echo ultrasound signals that are back-scattered by the region of interest, convert the echo ultrasound signals into electrical signals, and provide the electrical signals to the receiver 210. The receiver 210 may be configured to receive electrical signals from the elements 208, and provide the electrical signals to the receive beamformer 212. The receive beamformer 212 may apply delay times to the electrical signals received from the elements 208.

The user input device 214 may be configured to receive a user input, and provide the user input to the processor 216. For example, the user input device 214 may be a touch screen display, a keyboard, a keypad, a mouse, a button, a switch, a microphone, or the like. Additionally, or alternatively, the user input device 214 may be configured to sense information. For example, the user input device 214 may sense information from an electro-magnetic positioning system, an inertial measurement system, an accelerometer, a gyroscope, an actuator, or the like.

The processor 216 may be configured to perform the operations as described herein. For example, the processor 216 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. The processor 216 may be implemented in hardware, firmware, or a combination of hardware and software. The processor 216 may include one or more processors 216 configured to perform the operations described herein. For example, a single processor 216 may be configured to perform all of the operations described herein. Alternatively, multiple processors 216, collectively, may be configured to perform all of the operations described herein, and each of the multiple processors 216 may be configured to perform a subset of the operations descried herein. For example, a first processor 216 may perform a first subset of the operations described herein, a second processor 216 may be configured to perform a second subset of the operations described herein, etc.

The processor 216 may be configured to control the ultrasound probe 202 to acquire ultrasound data. The processor 216 may be configured to control which of the elements 208 are active, and control the shape of a beam emitted from the ultrasound probe 202. The processor 216 may generate ultrasound images for display. For example, the processor 216 may generate B-mode images, color Doppler images, M-mode images, color M-mode images, or the like. The ultrasound images may be 3D images, 2D images, single plane images, bi-plane images, three-plane images, multi-plane images, or the like. The ultrasound images may correspond to various anatomical planes (e.g., sagittal, coronal, and transverse) of the region of interest.

The display 218 may be configured to display information. For example, the display 218 may be a monitor, an LED display, a cathode ray tube, a projector display, a touchscreen, tablet computer, mobile phone, or the like. The display 218 may display ultrasound images based on the ultrasound data in real-time. For example, the display 218 may display the ultrasound images within one second, two seconds, five seconds, etc., of the ultrasound data being acquired by the ultrasound probe 202.

The memory 220 may be configured to store information and/or instructions for use by the processor 216. The memory 220 may be a non-transitory computer-readable medium. For example, the memory 220 may be a random access memory (RAM), a read only memory (ROM), and/or another type of dynamic or static storage device (e.g., a flash memory, a magnetic memory, and/or an optical memory) that stores information and/or instructions for use by the processor 216. The memory 220 may be configured to store instructions that, when executed by the processor 216, cause the processor 216 to perform the operations described herein.

The communication interface 222 may be configured to enable the processor 216 to communicate with other systems, such as via a wired connection, a wireless connection, or a combination of wired and wireless connections. For example, the communication interface 222 may include an Ethernet interface, an optical interface, a coaxial interface, an infrared interface, a radio frequency (RF) interface, a universal serial bus (USB) interface, a Wi-Fi interface, a cellular network interface, or the like.

The number and arrangement of the components of the ultrasound system 110 shown in FIG. 2 are provided as an example. In practice, the ultrasound system 110 may include additional components, fewer components, different components, or differently arranged components than those shown in FIG. 2. Additionally, or alternatively, a set of components (e.g., one or more components) of the ultrasound system 110 may perform one or more functions described as being performed by another set of components of the ultrasound system 110.

Figure 3:
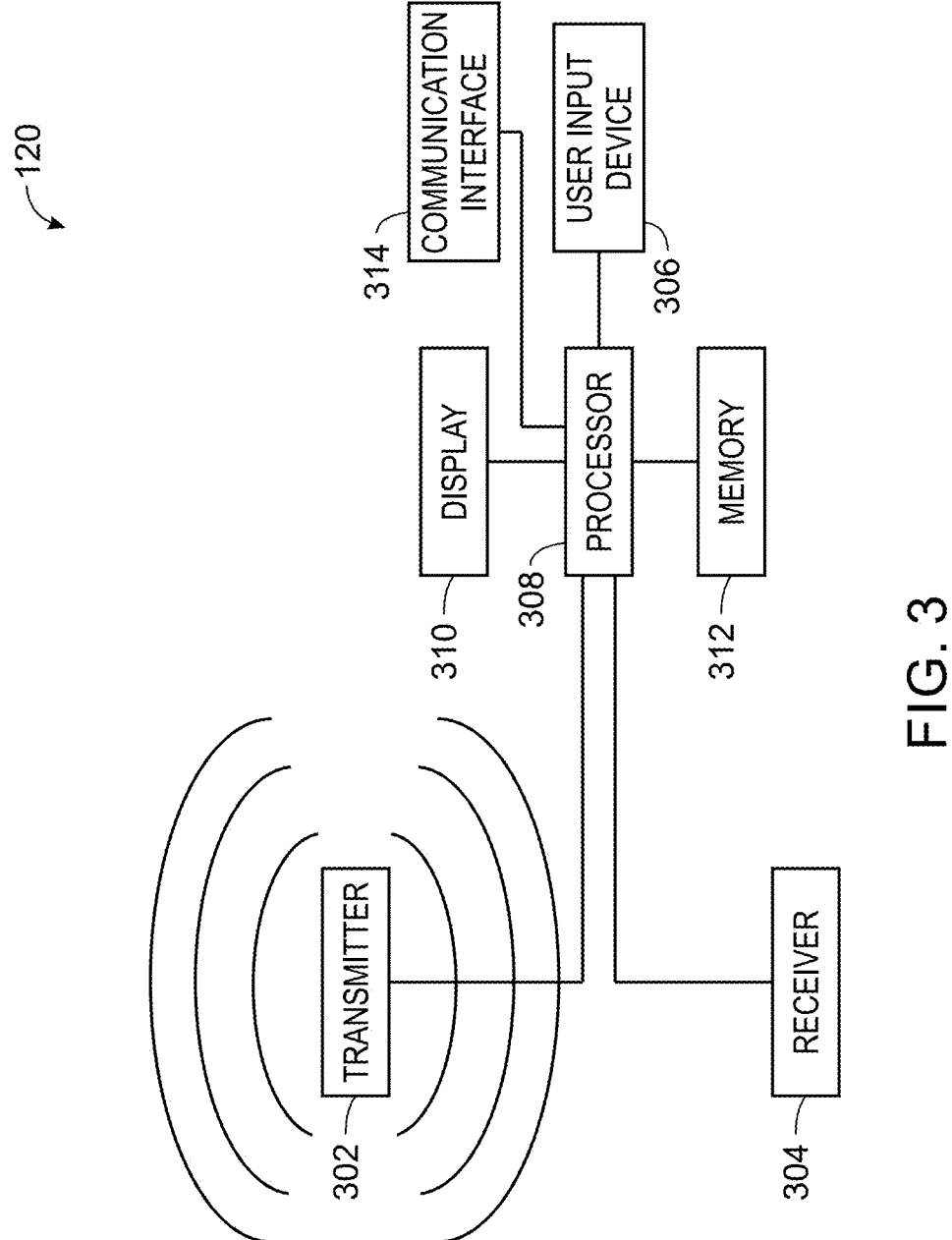
FIG. 3 is a diagram of an example tracking system for acquiring tracking data of a medical instrument located within a region of interest of a subject.

FIG. 3 is a diagram of example components of a tracking system 120. As shown in FIG. 3, the tracking system 120 may include a transmitter 302, a receiver 304, a user input device 306, a processor 308, a display 310, a memory 312, and a communication interface 314.

The transmitter 302 may be configured to generate a magnetic field. The receiver 304 may be configured to output a signal in response to the magnetic field generated by the transmitter 302. The processor 308 may receive the output signal from the receiver 304, and acquire tracking data that identifies a position and/or an orientation of the receiver 304. According to an embodiment, the receiver 304 may be attached to the ultrasound probe 202 to track a position and/or an orientation of the ultrasound probe 202. Alternatively, the receiver 304 may be attached to the medical instrument 140 to track a position and/or an orientation of the medical instrument 140. Alternatively, the receiver 304 may be attached to the feature in the region of interest.

The user input device 306 may be configured to receive a user input, and provide the user input to the processor 308. For example, the user input device 306 may be a touch screen display, a keyboard, a keypad, a mouse, a button, a switch, a microphone, or the like. Additionally, or alternatively, the user input device 306 may be configured to sense information. For example, the user input device 306 may sense information from an electro-magnetic positioning system, an inertial measurement system, an accelerometer, a gyroscope, an actuator, or the like.

The processor 308 may be configured to perform the operations as described herein. For example, the processor 308 may be a CPU, a GPU, an APU, a microprocessor, a microcontroller, a DSP, an FPGA, an ASIC, or the like. The processor 308 may be implemented in hardware, firmware, or a combination of hardware and software. The processor 308 may include one or more processors 308 configured to perform the operations described herein. For example, a single processor 308 may be configured to perform all of the operations described herein. Alternatively, multiple processors 308, collectively, may be configured to perform all of the operations described herein, and each of the multiple processors 308 may be configured to perform a subset of the operations descried herein. For example, a first processor 308 may perform a first subset of the operations described herein, a second processor 308 may be configured to perform a second subset of the operations described herein, etc.

The processor 308 may be configured to control the transmitter 302 to acquire tracking data. The processor 308 may be configured to control excitations of the transmitter 302 to generate a magnetic field. The processor 308 may acquire tracking data based on controlling the transmitter 302.

The display 310 may be configured to display information. For example, the display 310 may be a monitor, an LED display, a cathode ray tube, a projector display, a touchscreen, tablet computer, mobile phone, or the like. The display 310 may display the tracking data in real-time. For example, the display 310 may display the tracking data within one second, two seconds, five seconds, etc., of the tracking data being acquired.

The memory 312 may be configured to store information and/or instructions for use by the processor 308. The memory 312 may be a non-transitory computer-readable medium. For example, the memory 312 may be a RAM, a ROM, a flash memory, a magnetic memory, an optical memory, or the like. The memory 312 may be configured to store instructions that, when executed by the processor 308, cause the processor 308 to perform the operations described herein.

The communication interface 314 may be configured to enable the processor 308 to communicate with other systems, such as via a wired connection, a wireless connection, or a combination of wired and wireless connections. For example, the communication interface 314 may include an Ethernet interface, an optical interface, a coaxial interface, an infrared interface, an RF interface, a USB interface, a Wi-Fi interface, a cellular network interface, or the like.

The number and arrangement of the components of the tracking system 120 shown in FIG. 3 are provided as an example. In practice, the tracking system 120 may include additional components, fewer components, different components, or differently arranged components than those shown in FIG. 3. Additionally, or alternatively, a set of components (e.g., one or more components) of the tracking system 120 may perform one or more functions described as being performed by another set of components of the tracking system 120.

Although FIG. 3 depicts the tracking system 120 as being an electromagnetic tracking system, it should be understood that the embodiments herein are applicable to other types of tracking systems, such as optical tracking systems, acoustic tracking systems, ultrasound tracking systems, AI-based tracking methods, or the like.

Figure 4:
FIG. 4 is a diagram of an example preoperative imaging system for acquiring preoperative imaging data of a region of interest of a subject.

FIG. 4 is a diagram of an example preoperative imaging system 130 for acquiring preoperative imaging data of a region of interest of a subject. As shown in FIG. 4, the preoperative imaging system 130 may include a gantry 402, a rotational frame 404, an X-ray source 406, an X-ray detector 408, a table 410, a processor 412, a memory 414, a display 416, a user input device 418, a communication interface 420, a picture archiving and communications system (PACS) 422, and a server 424.

The processor 412 may be configured to control operations of the preoperative imaging system 130. For example, the processor 412 may be a CPU, a GPU, an APU, a microprocessor, a microcontroller, a DSP, an FPGA, an ASIC, or the like. The processor 412 may be implemented in hardware, firmware, or a combination of hardware and software. The processor 412 may include one or more processors 412 configured to perform the operations described herein. For example, a single processor 412 may be configured to perform all of the operations described herein. Alternatively, multiple processors 412, collectively, may be configured to perform all of the operations described herein, and each of the multiple processors 412 may be configured to perform a subset of the operations descried herein. For example, a first processor 412 may perform a first subset of the operations described herein, a second processor 412 may be configured to perform a second subset of the operations described herein, etc.

The processor 412 may be configured to control the gantry 402, movement of the rotational frame 404, the X-ray source 406, the X-ray detector 408, and movement of the table 410.

The memory 414 may be configured to store information and/or instructions for use by the processor 412. The memory 414 may be a non-transitory computer-readable medium. For example, the memory 414 may be a RAM, a ROM, a flash memory, a magnetic memory, an optical memory, or the like. The memory 414 may be configured to store instructions that, when executed by the processor 412, cause the processor 412 to perform the operations described herein.

The display 416 may be configured to display information. For example, the display 416 may be a monitor, an LED display, a cathode ray tube, a projector display, a touchscreen, tablet computer, mobile phone, or the like.

The user input device 418 may be configured to receive a user input, and provide the user input to the processor 412. For example, the user input device 418 may be a touch screen display, a keyboard, a keypad, a mouse, a button, a switch, a microphone, or the like. Additionally, or alternatively, the user input device 418 may be configured to sense information. For example, the user input device 418 may sense information from an electro-magnetic positioning system, an inertial measurement system, an accelerometer, a gyroscope, an actuator, or the like.

The communication interface 420 may be configured to enable the processor 412 to communicate with other devices, such as via a wired connection, a wireless connection, or a combination of wired and wireless connections. For example, the communication interface 420 may include an Ethernet interface, an optical interface, a coaxial interface, an infrared interface, an RF interface, a USB interface, a Wi-Fi interface, a cellular network interface, or the like. The PACS 422 may be configured to communicate with external systems and/or networks to permit users at various locations to access the medical image. The server 424 may be configured to store one or more models as described herein. For example, the server 424 may be an on-premises server, a cloud server, a virtual machine, or the like.

The number and arrangement of the components of the preoperative imaging system 130 shown in FIG. 4 are provided as an example. In practice, the preoperative imaging system 130 may include additional components, fewer components, different components, or differently arranged components than those shown in FIG. 4. Additionally, or alternatively, a set of components (e.g., one or more components) of the preoperative imaging system 130 may perform one or more functions described as being performed by another set of components of the preoperative imaging system 130.

FIG. 5 is a flowchart of an example process 500 for generating an ultrasound image of a region of interest of a subject including a medical instrument and a delineation of a predicted impact point of the medical instrument.

As shown in FIG. 5, the process 500 may include acquiring ultrasound data of a region of interest of a subject (operation 510). For example, the ultrasound system 110 may acquire ultrasound data of a region of interest of a subject.

According to an embodiment, the region of interest may be any region of a subject. For example, the region of interest may be the heart, the brain, the liver, a blood vessel, or the like. The subject may be a patient, an animal, a phantom, or the like. The region of interest may be a region that is associated with an interventional procedure involving the medical instrument 140. For example, the interventional procedure may be a medical procedure involving the medical instrument 140 being navigated in the region of interest. The ultrasound system 110 may acquire the ultrasound data during the interventional procedure. The ultrasound data may be 3D data, 2D data, single plane data, bi-plane data, three-plane data, multi-plane data, or the like.

As further shown in FIG. 5, the process 500 may include determining a position of a medical instrument in the region of interest of the subject (operation 520). For example, the ultrasound system 110 may determine a position of the medical instrument 140 in the region of interest of the subject.

According to an embodiment, the ultrasound system 110 may determine the position of the medical instrument 140 in the region of interest of the subject using ultrasound data acquired by the ultrasound system 110. For example, the ultrasound system 110 may acquire ultrasound data of the region of interest during the interventional procedure, and determine the position of the medical instrument 140 in the region of interest using a template matching technique (e.g., speckle tracking), a motion estimation technique, an image registration technique, an AI technique, or the like. Additionally, or alternatively, the ultrasound system 110 may determine the position of the feature in the region of interest using tracking data acquired by the tracking system 120. For example, the tracking system 120 may acquire tracking data of the medical instrument 140 during the interventional procedure and provide the tracking data to the ultrasound system 110, and the ultrasound system 110 may determine the position of the medical instrument 140 based on the tracking data.

According to an embodiment, the ultrasound system 110 may determine the position of the medical instrument 140 in the region of interest in substantially real-time during the interventional procedure involving the medical instrument 140. For example, the ultrasound system 110 may determine the position of the medical instrument 140 in the region of interest during the interventional procedure concurrently with the movement of the medical instrument 140 in the region of interest. As used herein, "substantially real-time" may refer to an event occurring within a threshold timeframe of another event, such as within 10 milliseconds, one second, two seconds, etc.

According to an embodiment, the position of the medical instrument 140 may identify a location of the medical instrument 140 and/or an orientation of the medical instrument 140. For example, the position of the medical instrument 140 in the region of interest may include a set of spatial coordinates of the medical instrument 140 in the coordinate system of the ultrasound system 110, and/or may include a set of angular coordinates of the medical instrument 140 in the coordinate system of the ultrasound system 110. Alternatively, the coordinate system may be associated with a different system, or systems, shown in FIG. 1.

According to an embodiment, the position of the medical instrument 140 may be associated with a specific portion, or a set of portions, of the medical instrument 140. For example, the position of the medical instrument 140 may be associated with a tip of the medical instrument 140, a distal end portion of the medical instrument 140, a radiopaque marker of the medical instrument 140, or the like.

As further shown in FIG. 5, the process 500 may include determining a predicted impact point of the medical instrument with respect to an anatomical feature of the region of interest of the subject based on the position of the medical instrument and the ultrasound data of the region of interest of the subject (operation 530). For example, the ultrasound system 110 may determine a predicted impact point of the medical instrument 140 with respect to an anatomical feature of the region of interest of the subject based on the position of the medical instrument 140 and the ultrasound data of the region of interest of the subject. Additionally, or alternatively, the ultrasound system 110 may determine the predicted impact point based on a position of the medical instrument 140 and a direction of movement of the medical instrument 140.

According to an embodiment, the predicted impact point of the medical instrument 140 with respect to an anatomical feature of the region of interest may be a point on an anatomical feature of the region of interest that the medical instrument 140 is pointed at based on the position of the medical instrument 140. Additionally, or alternatively, the predicted impact point of the medical instrument 140 may be a point on an anatomical feature of the region of interest that the medical instrument 140 would contact, or could contact, if the medical instrument 140 were to continue along a trajectory of the medical instrument 140 as defined by the position of the medical instrument 140. For example, if the position of the medical instrument 140 identifies that the medical instrument 140 is pointed at a mitral valve and/or is moving towards the mitral valve, then the predicted impact point may be the mitral valve. In other words, the predicted impact point may be a point on an anatomical feature that the medical instrument 140 is pointed at and/or may contact, or come into close proximity with, if the trajectory of the medical instrument 140 remains the same.

According to an embodiment, the ultrasound system 110 may determine the predicted impact point of the medical instrument 140 with respect to an anatomical feature of the region of interest using an image processing technique. For example, the ultrasound system 110 may determine the predicted impact point using a template matching technique, an image registration technique, an AI technique, an edge detection technique, or the like.

According to an embodiment, the ultrasound system 110 may determine the predicted impact point based on analyzing ultrasound data along the trajectory of the medical instrument 140. For example, the ultrasound system 110 may determine the trajectory of the medical instrument 140 based on the position of the medical instrument 140, and analyze the ultrasound data along the trajectory. As an example, the ultrasound system 110 may analyze image parameters along the trajectory of the medical instrument 140, and determine the predicted impact point based on the image parameters. The image parameters may include brightness, resolution, opacity, or the like. The ultrasound system 110 may analyze the image parameters, and determine the predicted impact point based on a change in the image parameters, an image parameter satisfying a threshold, a change in image parameters satisfying a threshold, or the like. As an example, an intensity profile of the ultrasound data along the trajectory may have a step-like profile where the intensity value is relatively low in a cavity and increases when the trajectory reaches an anatomical structure. The ultrasound system 110 may determine the predicted impact point based on the intensity profile. The predicted impact point may be in a direction of motion of the medical instrument 140. Alternatively, the predicted impact point may be offset at an oblique angle with respect to the direction of motion of the medical instrument 140.

According to an embodiment, the ultrasound system 110 may determine the predicted impact point based on respective positions of anatomical features as determined using an AI model, and the position of the medical instrument 140. For example, the ultrasound system 110 may input the ultrasound data into an AI model, and determine respective positions of anatomical features of the region of interest based on an output of the AI model. The ultrasound system 110 may determine the predicted impact point based on the respective positions of the anatomical features and the position of the medical instrument 140.

According to an embodiment, the ultrasound system 110 may determine the predicted impact point based on respective positions of anatomical features as determined using preoperative imaging data from the preoperative imaging system 130, and the position of the medical instrument 140. For example, the ultrasound system 110 may determine the respective positions of the anatomical features using preoperative imaging data, and determine the predicted impact point based on the respective positions of the anatomical features and the position of the medical instrument 140.

As further shown in FIG. 5, the process 500 may include generating an ultrasound image of the region of interest of the subject including the medical instrument and a delineation of the predicted impact point of the medical instrument (operation 540), and displaying the ultrasound image of the region of interest of the subject including the medical instrument and the delineation of the predicted impact point of the medical instrument (operation 550). For example, the ultrasound system 110 may generate an ultrasound image of the region of interest of the subject including the medical instrument 140 and a delineation of the predicted impact point of the medical instrument 140, and display the ultrasound image of the region of interest of the subject including the medical instrument 140 and the delineation of the predicted impact point of the medical instrument 140.

According to an embodiment, the delineation of the predicted impact point may be a visual indicator of the predicted impact point. For example, the delineation of the predicted impact point may allow an operator to assess the predicted impact point.

According to an embodiment, the delineation of the predicted impact point may be displayed differently than other portions of the ultrasound image. For example, a portion of the ultrasound image that is within the delineation of the predicted impact point may be rendered using image parameters that are different than image parameters of other portions of the ultrasound image that are not within the delineation of the predicted impact point. For example, a portion of the ultrasound image within the delineation of the predicted impact point may be displayed using a first color, a first brightness, a first opacity, a first resolution, or the like, and portions of the ultrasound image outside of the delineation of the predicted impact point may be displayed using a second color, a second brightness, a second opacity, a second resolution, or the like. Alternatively, the delineation of the predicted impact point may be an icon, a shape, a dot, a circle, a label, a bounding box, a highlighting, or the like, that identifies the predicted impact point.

According to an embodiment, the ultrasound system 110 may determine a size of the delineation, and generate the delineation based on the size. For example, the ultrasound system 110 may use a predetermined size, and generate the delineation to include the predetermined size. Alternatively, the ultrasound system 110 may receive a user input from an operator, and determine the size based on the user input. For example, the operator may set the size of the delineation, and/or may adjust the size of the delineation. Alternatively, the ultrasound system 110 may determine the size based on a size of the anatomical feature. For example, the ultrasound system 110 may determine the size of the delineation to cover the entire anatomical feature. Alternatively, the ultrasound system 110 may determine the size of the delineation based on a size of the medical instrument 140. For example, the ultrasound system 110 may determine a size of the medical instrument 140 using an image processing technique or based on information identifying the medical instrument 140 (e.g., a device identifier, a serial number, or the like), and determine the size of the delineation based on the size of the medical instrument 140. Alternatively, the ultrasound system 110 may determine the size of the delineation based on a distance between the medical instrument 140 and the anatomical feature. For example, if the medical instrument 140 is farther away from the anatomical feature, then the delineation may be larger than a situation where the medical instrument 140 is close to the anatomical feature.

According to an embodiment, the ultrasound system 110 may determine an image parameter of the delineation based on the underlying anatomical feature. For example, the ultrasound system 110 may display a delineation of a predicted impact point on a mitral valve differently than a delineation of a predicted impact point on myocardium. Alternatively, the ultrasound system 110 may determine an image parameter of the delineation based on a safety range of the anatomical feature. For example, the ultrasound system 110 may display a delineation of a predicted impact point around the His bundle using a red color, whereas the ultrasound system 110 may display a delineation of a predicted impact point on less susceptible cardiac tissue using a green, or yellow, color. Alternatively, the ultrasound system 110 may determine an image parameter of the delineation based on a target anatomical feature. For example, if the interventional procedure involves the closure of the left atrial appendage, then the ultrasound system 110 may display the delineation using a green color when the delineation encompasses the left atrial appendage, whereas the ultrasound system 110 may display the delineation using a red color when the delineation does not encompass the left atrial appendage.

According to an embodiment, the ultrasound system 110 may display a visual indicator extending from the medical instrument 140 to, or towards, the delineation of the predicted impact point. For example, the visual indicator may be a cone, a line, a rectangle, an arrow, or the like. The visual indicator may be transparent. The ultrasound system 110 may display blood signals within, or around, the visual indicator using an image parameter that is different than image parameters of other regions of the ultrasound image. In some instances, the ultrasound system 110 may display blood signals using the same image parameter as the delineation of the predicted impact point.

The ultrasound system 110 may display the ultrasound image of the region of interest of the subject including the medical instrument 140 and the delineation of the predicted impact point of the medical instrument 140, and may update the display as the operator navigates the medical instrument 140 around, and/or through, the region of interest. In this way, the operator may readily assess which anatomical features are located within the trajectory of the medical instrument 140, which allows the operator to position the medical instrument 140 at, or near, an intended position, and/or allows the operator to avoid susceptible anatomical features. Accordingly, some embodiments herein provide an improvement to ultrasound imaging and an improvement to the ultrasound images. Further, some embodiments herein improve subject safety during interventional procedures, reduce the time of interventional procedures, improve the efficacy of interventional procedures, etc.

Although FIG. 5 includes particular operations and a particular sequence of operations, it should be understood that other embodiments may include different operations and/or different arranged operations than as shown in FIG. 5.

FIGS. 6A-6D are diagrams of an example user interface 600 that displays ultrasound images of a region of interest of a subject including a medical instrument and a delineation of the predicted impact point of the medical instrument.

Figure 6A:
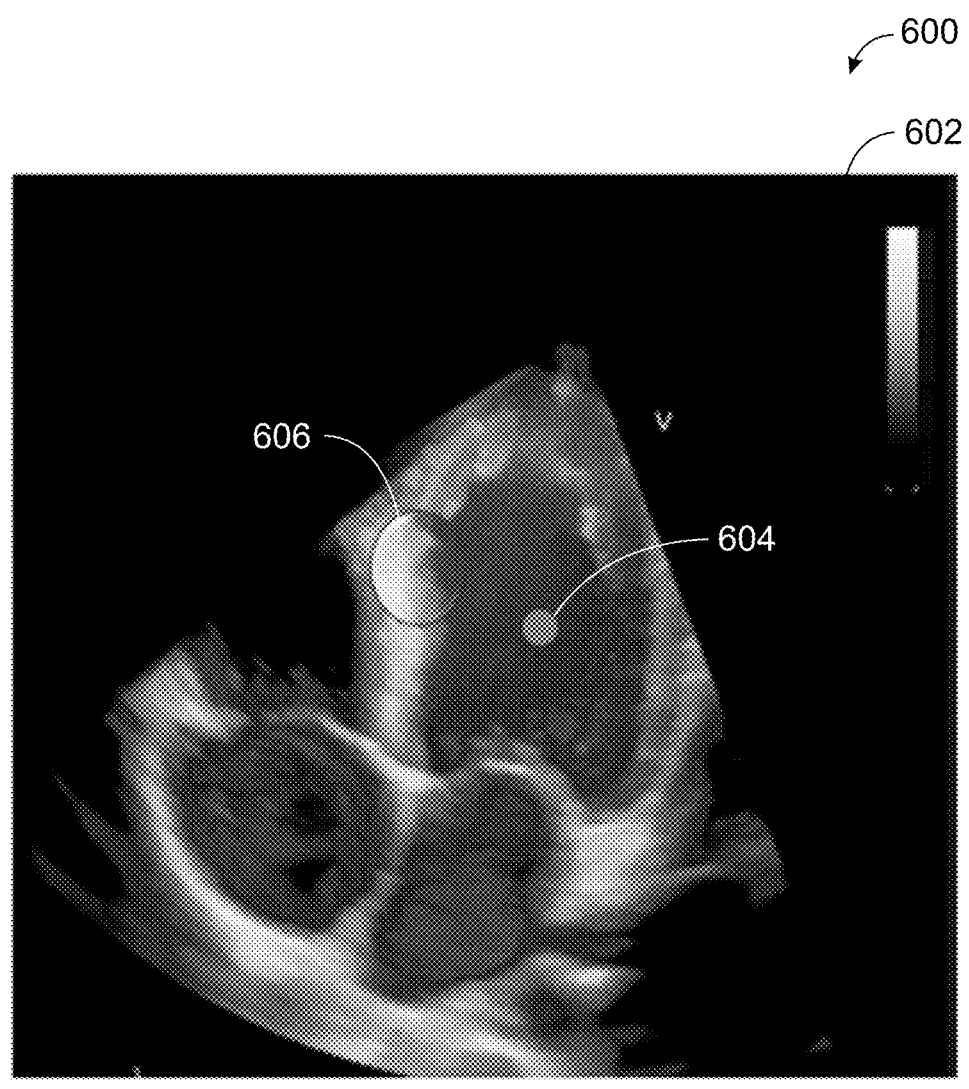
FIGS. 6A-6D are diagrams of an example user interface that displays ultrasound images of a region of interest of a subject including a medical instrument and a delineation of the predicted impact point of the medical instrument.

As shown in FIG. 6A, the ultrasound system 110 may display the user interface 600 including an ultrasound image 602. The ultrasound image 602 may include a region of interest (e.g., heart) of a subject. The ultrasound image 602 may display a visual indicator 604 for the medical instrument 140 that is positioned within the left ventricle of the heart of the subject. Further, the ultrasound image 602 may include a delineation 606 of a predicted impact point of the medical instrument 140 that is determined based on a position of the medical instrument 140.

Figure 6B:
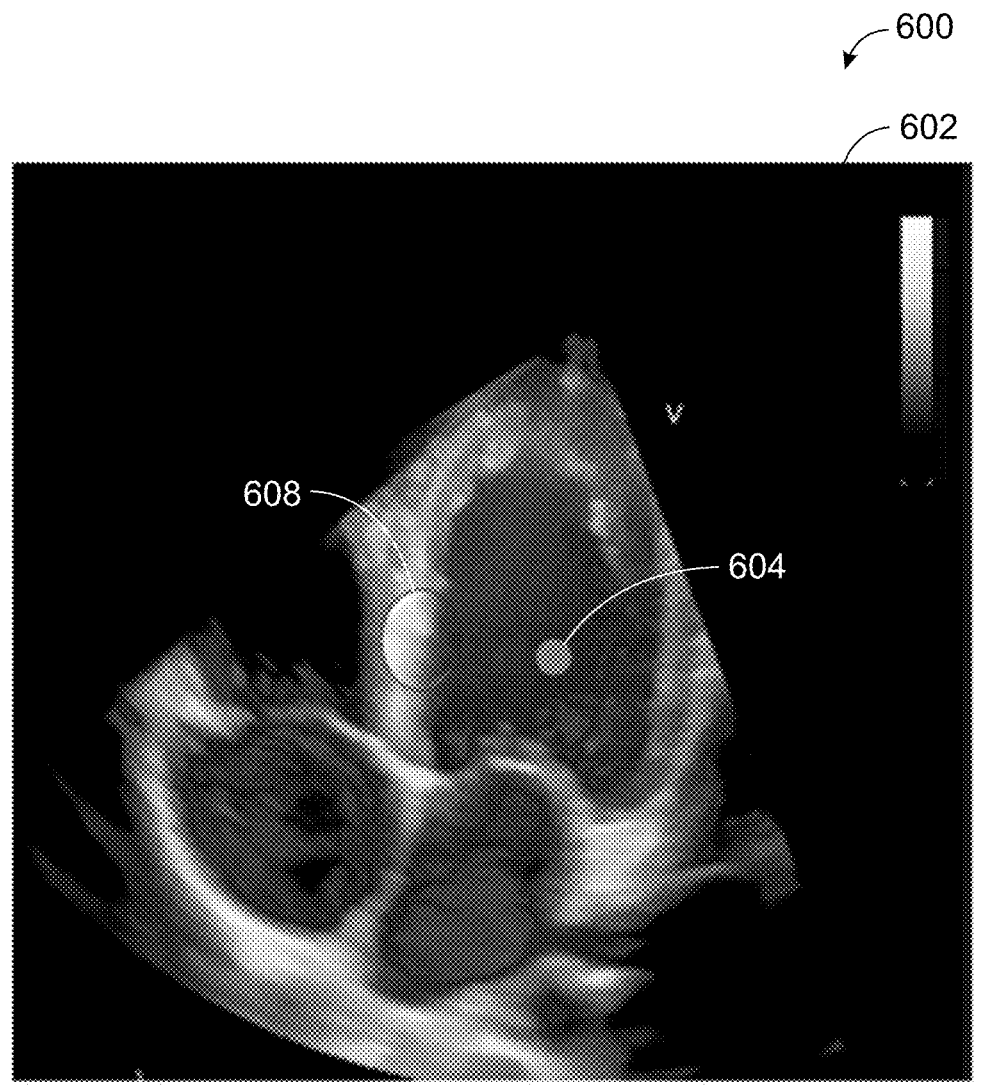

As shown in FIG. 6B, the ultrasound system 110 may display the user interface 600 including the ultrasound image 602. The ultrasound image 602 may include the region of interest of the subject. The ultrasound image 602 may display the visual indicator 604 for the medical instrument 140 that is positioned within the left ventricle of the heart of the subject. Further, the ultrasound image 602 may include a delineation 608 of a predicted impact point of the medical instrument 140. The delineation 608 may be positioned differently than the delineation 606 based on a change in the position of the medical instrument 140.

Figure 6C:
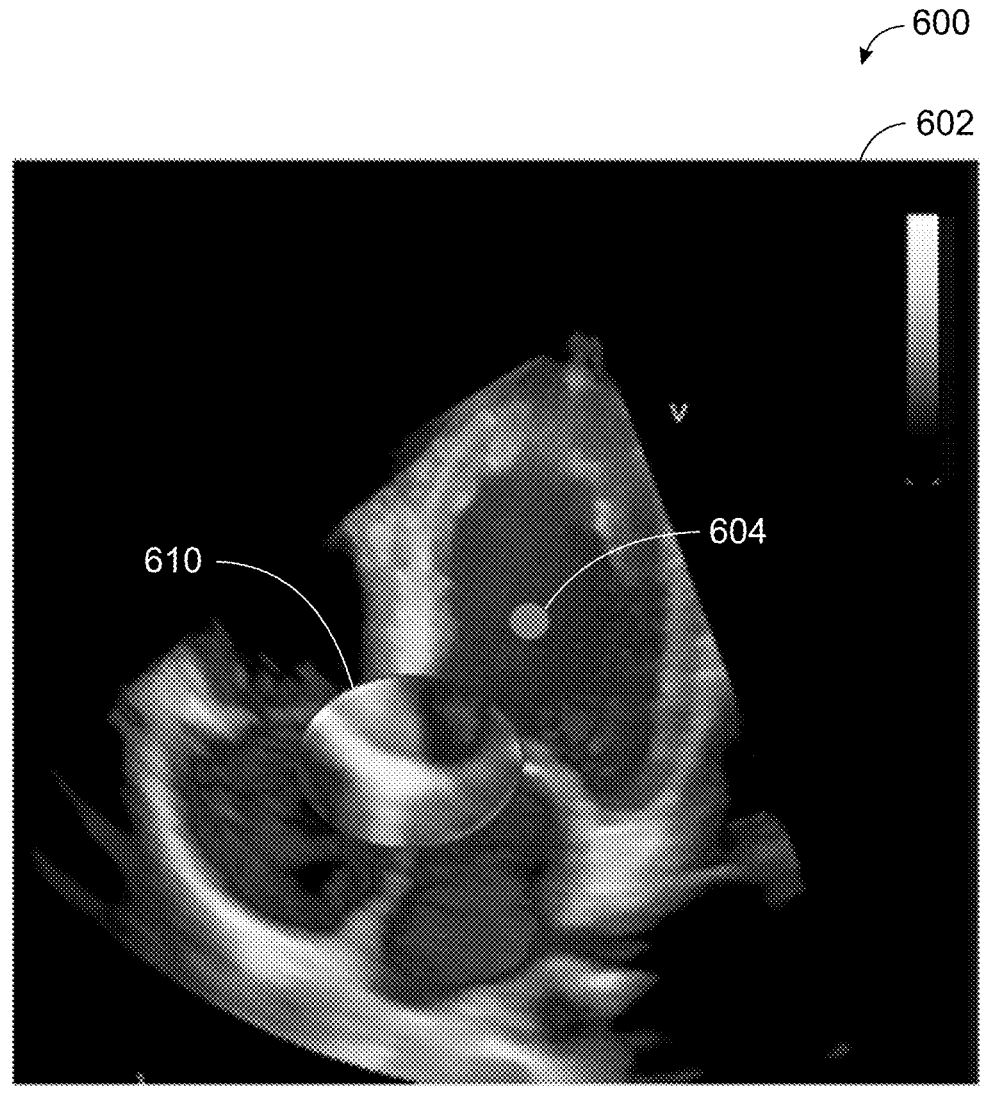

As shown in FIG. 6C, the ultrasound system 110 may display the user interface 600 including the ultrasound image 602. The ultrasound image 602 may include the region of interest of the subject. The ultrasound image 602 may display the visual indicator 604 for the medical instrument 140 that is positioned within the left ventricle of the heart of the subject. Further, the ultrasound image 602 may include a delineation 610 of a predicted impact point of the medical instrument 140. The delineation 610 may be positioned differently than the delineation 608 and the delineation 608 based on a change in the position of the medical instrument 140, and may be sized differently than the delineation 608 and the delineation 606 based on, for example, an adjustment by the operator of the medical instrument 140.

Figure 6D:
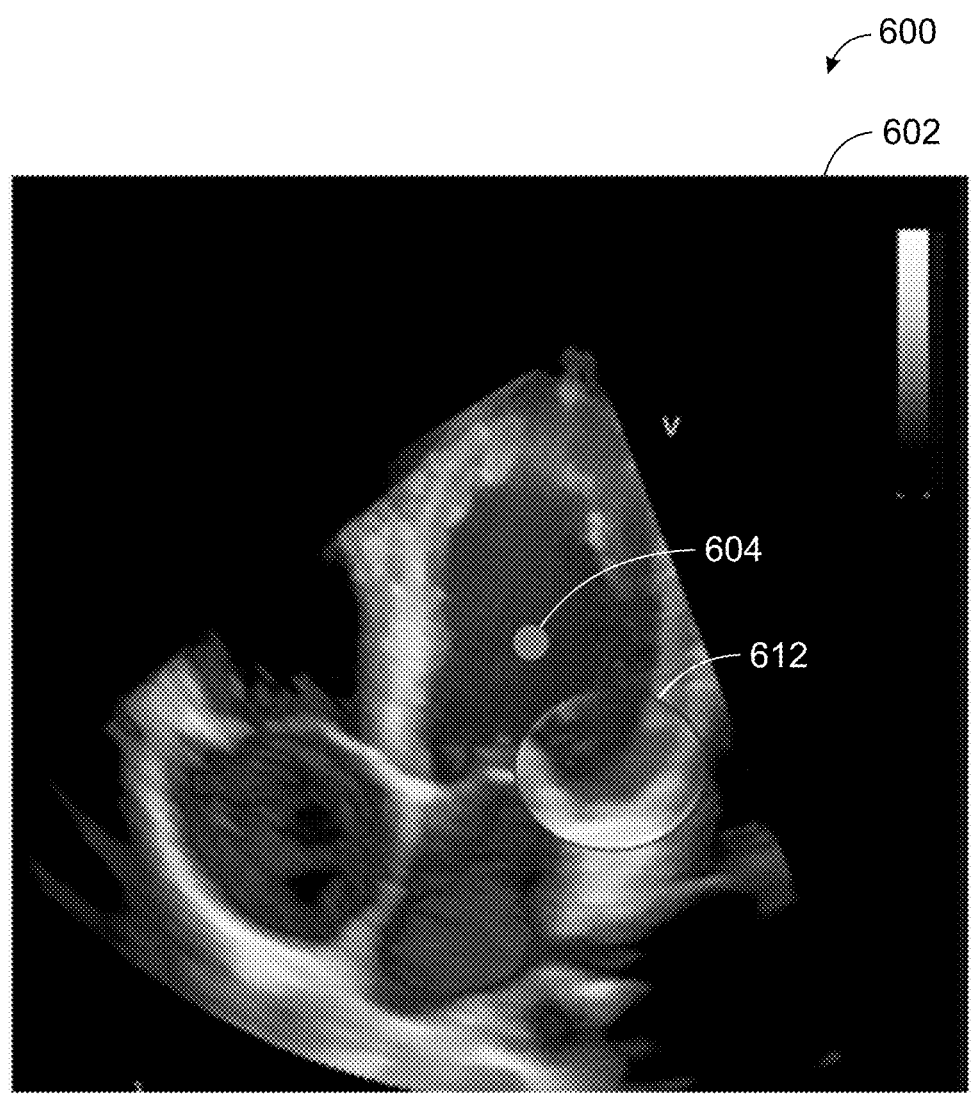

As shown in FIG. 6D, the ultrasound system 110 may display the user interface 600 including the ultrasound image 602. The ultrasound image 602 may include the region of interest of the subject. The ultrasound image 602 may display the visual indicator 604 for the medical instrument 140 that is positioned within the left ventricle of the heart of the subject. Further, the ultrasound image 602 may include a delineation 612 of a predicted impact point of the medical instrument 140. The delineation 612 may be positioned differently than the delineation 610, the delineation 608, and the delineation 606 based on a change in the position of the medical instrument 140.

Figure 7:
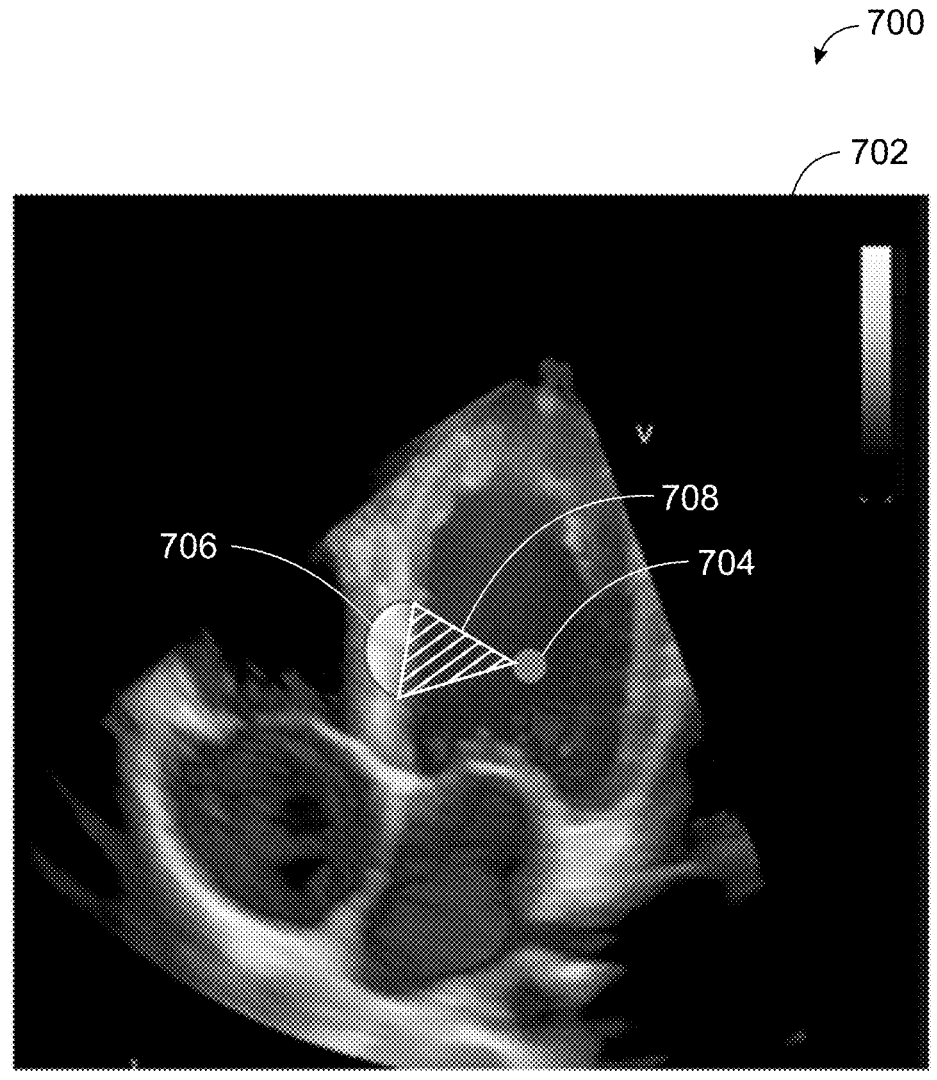
FIG. 7 is a diagram of an example user interface that displays an ultrasound image of a region of interest of a subject including a medical instrument, a delineation of a predicted impact point of the medical instrument, and a visual indicator extending from the medical instrument to the delineation of the predicted impact point.

FIG. 7 is a diagram of an example user interface 700 that displays an ultrasound image of a region of interest of a subject including a medical instrument, a delineation of a predicted impact point of the medical instrument, and a visual indicator extending from the medical instrument to the delineation of the predicted impact point.

As shown in FIG. 7, the ultrasound system 110 may display the user interface 700 including an ultrasound image 702. The ultrasound image 702 may include a region of interest (e.g., heart) of a subject. The ultrasound image 702 may display a visual indicator 704 for the medical instrument 140 that is positioned within the left ventricle of the heart of the subject. Further, the ultrasound image 702 may include a delineation 706 of a predicted impact point of the medical instrument 140 that is determined based on a position of the medical instrument 140. Further still, the ultrasound image 702 may include a visual indicator 708 that extends from the visual indicator 704 for the medical instrument 140 to the delineation 706 of the predicted impact point of the medical instrument 140. The visual indicator 708 may be cone-shaped, and may extend from the visual indicator 704 to the delineation 706 of the predicted impact point of the medical instrument 140. Blood signals within the visual indicator 708 may be displayed using a different image parameter than blood signals not within the visual indicator 708. The ultrasound system 110 may automatically update the delineation 706 of the predicted impact point, the visual indicator 704, and/or the visual indicator 708 as the medical instrument 140 is navigated, or steered, through the region of interest.

FIG. 8 is a flowchart of an example process 800 for generating an ultrasound image of a region of interest of a subject including a view that is substantially perpendicular to a longitudinal axis of a medical instrument in the region of interest.

As shown in FIG. 8, the process 800 may include acquiring ultrasound data of a region of interest of a subject (operation 810). For example, the ultrasound system 110 may acquire ultrasound data of a region of interest of a subject. The ultrasound system 110 may acquire the ultrasound data of the region of interest of the subject in a similar manner as described above with respect to operation 510 of FIG. 5.

As further shown in FIG. 8, the process 800 may include determining a position of a medical instrument in the region of interest of the subject (operation 820). For example, the ultrasound system 110 may determine a position of a medical instrument 140 in the region of interest of the subject. The ultrasound system 110 may determine a position of a medical instrument 140 in the region of interest of the subject in a similar manner as described above with respect to operation 520 of FIG. 5.

As further shown in FIG. 8, the process 800 may include generating an ultrasound image of the region of interest that includes a view that is substantially perpendicular to a longitudinal axis of the medical instrument based on the position of the medical instrument (operation 830), and displaying the ultrasound image of the region of interest of the subject (operation 840). For example, the ultrasound system 110 may generate an ultrasound image of the region of interest that includes a view that is substantially perpendicular to a longitudinal axis of the medical instrument 140 based on the position of the medical instrument, and displaying the ultrasound image of the region of interest of the subject.

According to an embodiment, the ultrasound system 110 may determine a plane that is substantially perpendicular to a longitudinal axis of the medical instrument 140 based on the position of the medical instrument. "Substantially perpendicular" may refer to being 90°, 91°, 93°, 96°, 100°, or the like, with respect to the longitudinal axis of the medical instrument 140. Although the embodiments herein describe a view that is "substantially perpendicular" to the longitudinal axis of the medical instrument 140, the ultrasound system 110 may determine a plane that is oblique to the longitudinal axis of the medical instrument 140.

According to an embodiment, the ultrasound system 110 may generate an ultrasound image that includes a view that is substantially perpendicular to a longitudinal axis of the medical instrument 140 based on the plane. For example, the ultrasound system 110 may render the ultrasound image such that the view appears to be from the viewpoint of the tip of the medical instrument 140.

According to an embodiment, the ultrasound image may a 3D ultrasound image or a 4D ultrasound image, and the ultrasound image may include a view that is a slice of the 3D ultrasound data or the 4D ultrasound data that is substantially perpendicular or oblique to a longitudinal axis of the medical instrument 140 based on the position of the medical instrument 140 in the region of interest of the subject.

According to an embodiment, the ultrasound system 110 may update the view of the ultrasound image as the medical instrument 140 is moved through the region of interest. For example, the ultrasound system 110 may update the anterior and/or posterior views based on movement of the medical instrument 140. The ultrasound system 110 may update the views based on a trajectory of the medical instrument 140. The ultrasound system 110 may determine the trajectory using a template matching technique, a motion estimation technique, or the like. As a specific example, the ultrasound system 110 may matching blocks within a search window of reference frame and a current frame. As another specific example, the ultrasound system 110 may register the medical instrument 140 in consecutive frames. The ultrasound system 110 may determine a motion vector, and determine the trajectory based on the motion vector.

According to an embodiment, the ultrasound system 110 may display a visual indicator that extends from the medical instrument 140, and that is displayed using a different image parameter than as compared to other portions of the ultrasound image. For example, the visual indicator may include an increased brightness, an increased resolution, a different opacity, or the like, than as compared to other portions of the ultrasound image.

Although FIG. 8 includes particular operations and a particular sequence of operations, it should be understood that other embodiments may include different operations and/or differently arranged operations than as shown in FIG. 8.

Figure 11:

FIGS. 9-11 are diagrams of example user interfaces 900, 1000, and 1100 that display an ultrasound image of a region of interest of a subject including a view that is substantially perpendicular to a longitudinal axis of a medical instrument in the region of interest.

As shown in FIG. 9, the user interface 900 may display an ultrasound image 902 corresponding to a posterior view of the medical instrument 140 as the medical instrument 140 moves towards an apex of the left ventricle. As further shown in FIG. 9, the user interface 900 may display an ultrasound image 904 corresponding to an anterior view of the medical instrument 140 as the medical instrument 140 moves towards the apex of the left ventricle.

As shown in FIG. 10, the user interface 1000 may display an ultrasound image 1002 corresponding to a posterior view of the medical instrument 140 as the medical instrument 140 moves towards a posterior cardiac wall of the left ventricle. As further shown in FIG. 10, the user interface 1000 may display an ultrasound image 1004 corresponding to an anterior view of the medical instrument 140 as the medical instrument 140 moves towards the posterior cardiac wall of the left ventricle.

As shown in FIG. 11, the user interface 1100 may display an ultrasound image 1102 corresponding to a posterior view of the medical instrument 140 as the medical instrument 140 moves towards an anterior cardiac wall of the left ventricle. As further shown in FIG. 11, the user interface 1100 may display an ultrasound image 1104 corresponding to an anterior view of the medical instrument 140 as the medical instrument 140 moves towards the anterior cardiac wall of the left ventricle.

Although the embodiments herein describe the usage of ultrasound data, it should be understood that the embodiments herein are applicable to other types of medical images and imaging modalities. For example, the embodiments herein may be implemented using MRI images, CT images, PET images, X-ray images, or the like.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A system comprising:
a memory configured to store instructions; and
one or more processors configured to execute the instructions to:
   acquire ultrasound data of a heart of a subject;
   determine a trajectory of a medical instrument in a cavity of the heart of the subject;
   analyze brightness of the ultrasound data along the trajectory of the medical instrument;
   determine a predicted impact point of the medical instrument with respect to an anatomical feature of the heart of the subject based on the brightness of the ultrasound data along the trajectory changing from a first value in the cavity to a second value when the trajectory reaches the anatomical feature of the heart of the subject;
   generate an ultrasound image of the heart of the subject including the medical instrument and a delineation of the predicted impact point of the medical instrument; and
   display the ultrasound image of the heart of the subject including the medical instrument and the delineation of the predicted impact point of the medical instrument.

2. The system of claim 1, wherein the one or more processors are further configured to:
   receive a user input that indicates a size of the delineation of the predicted impact point of the medical instrument,
   wherein the displaying the ultrasound image comprises displaying the ultrasound image including the delineation of the predicted impact point of the medical instrument having the size indicated by the user input.

3. The system of claim 1, wherein the ultrasound data is three-dimensional (3D) ultrasound data or four-dimensional (4D) ultrasound data, wherein the ultrasound image is a 3D ultrasound image or a 4D ultrasound image, and wherein the one or more processors are configured to generate the ultrasound image that includes a view that is a slice of the 3D ultrasound data or the 4D ultrasound data that is substantially perpendicular or oblique to a longitudinal axis of the medical instrument based on a position of the medical instrument in the heart of the subject.

4. The system of claim 1, wherein the one or more processors are configured to determine the predicted impact point of the medical instrument with respect to the anatomical feature of the heart of the subject based on a position and direction of movement of the medical instrument and the ultrasound data of the heart of the subject.

5. The system of claim 1, wherein a first portion of the ultrasound image within the delineation of the predicted impact point include a first color, a first brightness, or a first opacity, and wherein a second portion outside of the delineation of the predicted impact point include a second color that is different than the first color, a second brightness that is different than the first brightness, or a second opacity that is different than the first opacity.

6. The system of claim 1, wherein the one or more processors are further configured to:
   determine a movement of the medical instrument in the heart; and
   update the delineation of the predicted impact point of the medical instrument based on the movement of the medical instrument in the heart.

7. The system of claim 1, wherein the one or more processors are configured to generate the ultrasound image of the heart of the subject to include a transparent cone that extends from a tip of the medical instrument to the predicted impact point of the medical instrument, and display first blood signals within the transparent cone using a first image parameter that is different than a second image parameter of second blood signals outside of the transparent cone.

8. A method comprising:
   acquiring ultrasound data of a heart of a subject;
   determining a trajectory of a medical instrument in a cavity of the heart of the subject;
   analyzing brightness of the ultrasound data along the trajectory of the medical instrument;
   determining a predicted impact point of the medical instrument with respect to an anatomical feature of the heart of the subject based on the brightness of the ultrasound data along the trajectory changing from a first value in the cavity to a second value when the trajectory reaches the anatomical feature of the heart of the subject;
   generating an ultrasound image of the heart of the subject including the medical instrument and a delineation of the predicted impact point of the medical instrument; and
   displaying the ultrasound image of the heart of the subject including the medical instrument and the delineation of the predicted impact point of the medical instrument.

9. The method of claim 8, further comprising:
   receiving a user input that indicates a size of the delineation of the predicted impact point of the medical instrument,
   wherein the displaying the ultrasound image comprises displaying the ultrasound image including the delineation of the predicted impact point of the medical instrument having the size indicated by the user input.

10. The method of claim 8, wherein the generating the ultrasound image comprises generating the ultrasound image that includes a view that is substantially perpendicular or oblique to a longitudinal axis of the medical instrument based on a position of the medical instrument in the heart of the subject.

11. The method of claim 8, wherein the determining the predicted impact point comprises determining the predicted impact point of the medical instrument with respect to the anatomical feature of the heart based on an intensity profile of the ultrasound data along the trajectory extending from the medical instrument to the anatomical feature.

12. The method of claim 8, wherein a first portion of the ultrasound image within the delineation of the predicted impact point include a first color, a first brightness, or a first opacity, and wherein a second portion outside of the delineation of the predicted impact point include a second color that is different than the first color, a second brightness that is different than the first brightness, or a second opacity that is different than the first opacity.

13. The method of claim 8, further comprising:
   determining a movement of the medical instrument in the heart; and
   updating the delineation of the predicted impact point of the medical instrument based on the movement of the medical instrument in the heart.

14. The method of claim 8, wherein the generating the ultrasound image comprises generating the ultrasound image of the heart of the subject to include a cone that extends from a tip of the medical instrument to the predicted impact point of the medical instrument, and display first blood signals within the cone using a first image parameter that is different than a second image parameter of second blood signals outside of the cone.

15. A non-transitory computer-readable medium storing instructions that, when executed by one or more processors, cause the one or more processors to:
   acquire ultrasound data of a heart of a subject;
   determine a trajectory of a medical instrument in a cavity of the heart of the subject;
   analyze brightness of the ultrasound data along the trajectory of the medical instrument;
   determine a predicted impact point of the medical instrument with respect to an anatomical feature of the heart of the subject based on the brightness of the ultrasound data along the trajectory changing from a first value in the cavity to a second value when the trajectory reaches the anatomical feature of the heart of the subject; and
   display an ultrasound image of the heart of the subject including the medical instrument and a delineation of the predicted impact point of the medical instrument.

16. The non-transitory computer-readable medium of claim 15, wherein the instructions further cause the one or more processors to:
   receive a user input that indicates a size of the delineation of the predicted impact point of the medical instrument,
   wherein the displaying the ultrasound image comprises displaying the ultrasound image including the delineation of the predicted impact point of the medical instrument having the size indicated by the user input.

17. The non-transitory computer-readable medium of claim 15,
   wherein the instructions that cause the one or more processors to generate the ultrasound image cause the one or more processors to generate the ultrasound image that includes a view that is substantially perpendicular or oblique to a longitudinal axis of the medical instrument based on a position of the medical instrument in the heart of the subject.

18. The non-transitory computer-readable medium of claim 15, wherein the instructions that cause the one or more processors to determine the predicted impact point cause the one or more processors to determine the predicted impact point of the medical instrument with respect to the anatomical feature of the heart based on an intensity profile of the ultrasound data along the trajectory extending from the medical instrument to the anatomical feature.

19. The non-transitory computer-readable medium of claim 15, wherein a first portion of the ultrasound image within the delineation of the predicted impact point include a first color, a first brightness, or a first opacity, and wherein a second portion outside of the delineation of the predicted impact point include a second color that is different than the first color, a second brightness that is different than the first brightness, or a second opacity that is different than the first opacity.

20. The non-transitory computer-readable medium of claim 15, wherein the instructions further cause the one or more processors to:
   determine a movement of the medical instrument in the heart; and
   update the delineation of the predicted impact point of the medical instrument based on the movement of the medical instrument in the heart.

* * * * *